United States Patent [19]
Daikuzono

[11] Patent Number: 5,738,679
[45] Date of Patent: Apr. 14, 1998

[54] APPARATUS FOR LASER TREATMENT FOR LIVING TISSUE

[75] Inventor: Norio Daikuzono, Cincinnati, Ohio

[73] Assignee: S.L.T. Japan Company Limited, Tokyo, Japan

[21] Appl. No.: 670,361

[22] Filed: Jun. 26, 1996

[51] Int. Cl.$^6$ ................................................ A61B 17/36
[52] U.S. Cl. ............................................. 606/11; 606/9
[58] Field of Search ................................ 606/4, 5, 6, 13, 606/14, 10, 11, 12, 17, 18

[56] References Cited

U.S. PATENT DOCUMENTS

| | | | |
|---|---|---|---|
| 5,246,435 | 9/1993 | Bille et al. | 606/6 |
| 5,360,424 | 11/1994 | Klopotek | 606/4 |
| 5,364,390 | 11/1994 | Taboada et al. | 606/10 |
| 5,437,657 | 8/1995 | Epstein | 606/4 |

Primary Examiner—Jennifer Bahr
Assistant Examiner—Sonya Harris-Ogugua
Attorney, Agent, or Firm—Andrus, Sceales, Starke & Sawall

[57] ABSTRACT

The present invention is used for irradiating the entire of nevus on the skin with laser light uniformly and efficiently to remove it.

A laser treating apparatus for living tissue the present invention comprises a laser light generator; a main optical fiber for receiving the laser light from said laser light generator to irradiate the surface of the living tissue with the laser light; a plurality of optical fiber bundle which is annularly disposed around the main optical fiber and having the front ends facing the surface of the tissue; laser light switching means between said laser light generator and said laser light transmitting means; a first light quantity detecting means for measuring the quantity light which has been emitted from said laser light transmitting means and has been reflected on the surface of the tissue; second light quantity of detecting means for measuring the quantity of laser light reflected on a predetermined area on said surface of the tissue; and irradiation control means for impinging the laser light from said laser light generator upon said laser light transmitting means by actuating said switching means when the irradiation of laser light is determined necessary based upon the ratio (Im/Ir) of the second light quantity Im measured by said second light quantity detecting means to the first light quantity Ir measured by said first light quantity detecting means which is used as an index representing whether or not unirradiated area is present, reirradiation is necessary.

10 Claims, 9 Drawing Sheets

APPARATUS FOR LASER TREATMENT FOR LIVING TISSUE

TECHNICAL FIELD OF THE INVENTION

The present invention relates to an apparatus for laser treatment for living tissue, which is particularly used for modification of the tissue, for example, removal of the nevus by irradiating the surface of the living tissue with laser light.

BACKGROUND OF THE INVENTION

The nevus is the skin tissue on which melanism takes place. Various methods of eliminating the nevus have heretofore been known, including a method of chemically peeling the nevus area on which hydrogen peroxide is applied and a method of vaporization of the nevus area by being irradiated with laser light.

However, it is very difficult to completely eliminate the nevus by these methods. Although a method of eliminating the nevus by irradiating it with laser light has attracted attention owing to its future, a high power laser light L is required, which is impinged upon the surface of the tissue M as shown in FIG. 11 since a high proportion of the impinged laser light will be scattered in a rearward direction. A high proportion of the laser light which has penetrated into the tissue will be scattered therein, resulting in that there is a risk that the unwanted tissue other than the target tissue might be damaged. Since the distribution of the strength of the laser light is such that the laser light induces higher temperature in a core of an optical fiber and lower temperatures in the periphery thereof, uniform vaporization of the tissue can not be achieved. Since identification of the laser light irradiation position depends only upon visual monitoring, failure of irradiation of some of the target area is liable to occur.

Accordingly, in order to irradiate the target tissue area uniformly and efficiently, the present inventor proposed in Ser. No. 08/625,313; a system and method of treating the living tissue by irradiating it with laser light, comprising the steps of: applying on the surface of the living tissue a liquid target material including laser light absorbing powders having a particle size of not higher than 40 µm and a dispersant in which said powders are dispersed so that the thickness of the applied film becomes not higher than 40 µm; and irradiating the target material area of the tissue with laser light.

In this laser treating system, a liquid target material comprising laser absorbing powders which are dispersed in a dispersing medium, preferably laser absorbing powders having a particle size of 40 µm or less, which are dispersed in water and alcohol is applied on the surface of the tissue M as shown at T in FIG. 5.

The target material T is applied on a target tissue, for example, the nevus to be eliminated with a felt pen. The laser light L which has transmitted through the optical fiber from the laser light generator is emitted toward the target applied area from the front end of the optical fiber.

The laser light L which has collided with the target material T will be absorbed by the laser light absorbing powders contained in the target material T so that it will be converted into thermal energy. As a result, the temperature of the laser light irradiated tissue elevates momentarily to high temperature such as 800° to 1000° C., so that vaporization of the tissue takes place. As a result, the original skin condition can be viewed at the irradiated spots while the target material which has black color remains at the unirradiated spots as shown in FIG. 6. An operator can determine that the black area has not been irradiated and then conduct laser light irradiation of the black area at next stage (refer to FIG. 7). This enables the operator to easily conduct the laser light irradiation over the entire desired area.

However, the diameter of the unit irradiation area R is as small as about 3 mm. It is very hard for a surgical operator to irradiate the unirradiated area with a fine laser light while visually observing it. A great burden is imposed upon the operator. As a result, several unirradiated areas may remain.

It is therefore an object of the present invention to provide a method and system which can mitigate the burden to an operator by conducting the laser irradiation on an optical basis, not visual basis.

It is another object of the present invention to prevent the unirradiated area from occurring and to irradiate the entire target area.

SUMMARY OF THE INVENTION

In accordance with the present invention, there is provided in an apparatus for modifying the surface of living tissue by irradiating it with laser light, a laser treating apparatus for living tissue, comprising: a laser light generator; a laser light transmitting means for receiving the laser light from said laser light generator to impinge it upon the surface of the tissue; switching means between said laser light generator and said laser light transmitting means; a first light quantity detecting means for measuring the quantity of light which has been emitted from said laser light transmitting means and has been reflected on the surface of the tissue; second light quantity detecting means for measuring the quantity of laser light reflected on a predetermined area on said surface of the tissue; and irradiation control means for impinging the laser light from said laser light generator upon said laser light transmitting means by actuating said switching means when the irradiation of laser light is determined necessary based upon the ratio (Im/Ir) of the second light quantity Im measured by said second light quantity detecting means to the first light quantity Ir measured by said first light quantity detecting means which is used as an index representing whether or not an unirradiated area is present, or irradiation is necessary.

There is also provided in an apparatus for modifying the surface of living tissue by irradiating it with laser light, a laser treating apparatus for living tissue, comprising: a laser light generator; a main optical fiber for receiving the laser light from said laser light generator to irradiate the surface of the living tissue with the laser light; a plurality of optical fiber bundle which are annularly disposed around the main optical fiber and having the front ends facing the surface of the tissue; laser light switching means between said laser light generator and said laser light transmitting means; a first light quantity detecting means for measuring the quantity of light which has been emitted from said laser light transmitting means and has been reflected on the surface of the tissue; second light quantity detecting means for measuring the quantity of laser light reflected on a predetermined area on said surface of the tissue; and irradiation control means for impinging the laser light from said laser light generator upon said laser light transmitting means by actuating said switching means when the irradiation of laser light is determined necessary based upon the ratio (Im/Ir) of the second light quantity Im measured by said second light quantity detecting means to the first light quantity Ir measured by said first light quantity detecting means which is used as an index representing whether or not an unirradiated area is present, or irradiation is necessary.

Said first and second laser light switching means may be provided on the sides of said laser light generator and said laser light transmitting means, respectively between said laser light generator and said laser light transmitting means. Said first laser light switching means may be actuated in association with a foot switch for an operator. Said second laser light switching means may be actuated by said irradiation control means.

A condenser lens for condensing the reflected laser light to said optical fiber bundles may be provided on the side of the front ends of said optical fiber bundles.

Said condenser lens may be formed at the center thereof with a through-hole, into which said main optical fiber is inserted.

Said main optical fiber and said optical fiber bundles may be secured to a holder which is held by an operator.

Said main optical fiber may be movably supported by the holder so that the separation distance between the optical fiber and said tissue surface is adjustable.

Said main optical fiber and said optical fiber bundle may be secured to the holder. Said holder may be held in a holder fitting of an X-Y translating apparatus which holder fitting is movable along orthogonal X and Y axes in a plane parallel with the surface of the tissue.

A target material comprising laser light absorbing powders having a particle size of 40 μm or less which are dispersed in a dispersing medium may be applied to a coating thickness of 40 μm or less on the surface of said tissue.

PREFERRED EMBODIMENT OF THE INVENTION

Now, the present invention will be described, with reference to the drawings, by way of an embodiment in which the nevus on the skin of the tissue M is eliminated.

Figure 1:
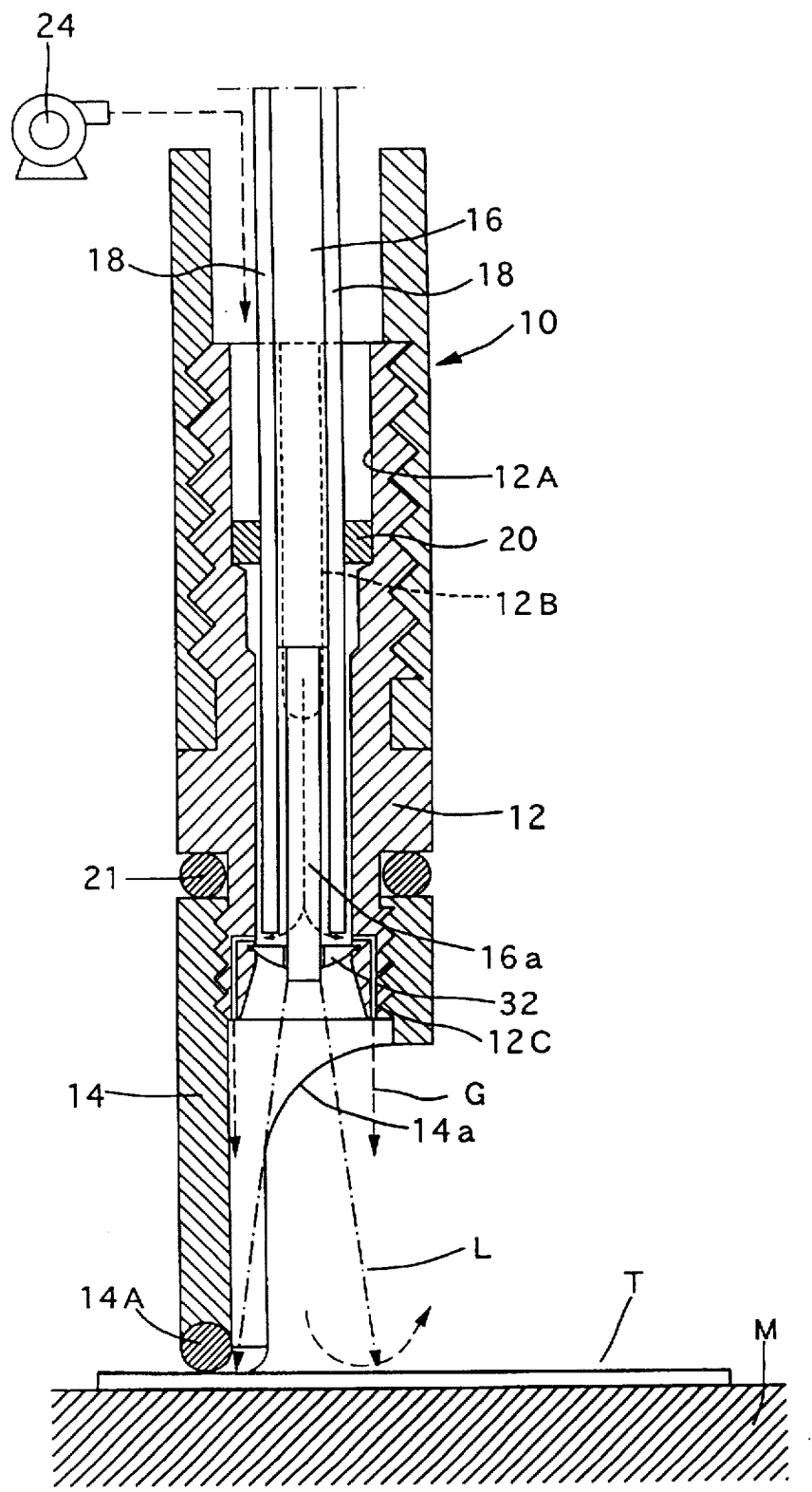
FIG. 1 is a schematic view showing an example of a laser light irradiating device of the present invention.
Figure 2:
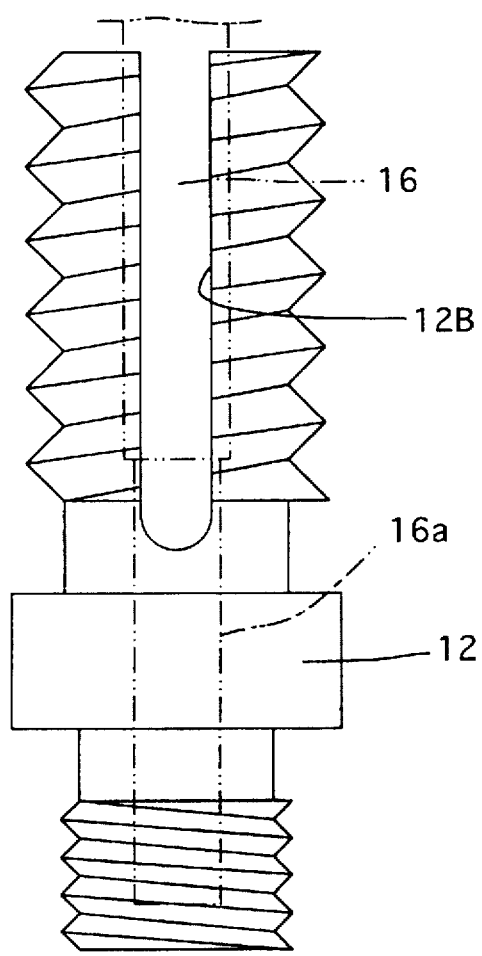
FIG. 2 is a front view showing a connector for the device shown in FIG. 1.

In the present invention, a connector 12 is threadably connected with the front end of a handpiece 10 (only the front end portion thereof is shown in FIG. 1) which is gripped by a surgical operator. A distance keeping front terminal fitting 14 is threadably connected with the connector 12 at the front end thereof. The handpiece 10, the connector 12 and the distance keeping front terminal fitting 14 constitute a holder of the present invention.

Front end portions of an optical fiber 16 and optical fiber bundles 18 are inserted into a through-hole 12A of the connector 12. A clad is separated from the front end portion of the optical fiber 16 so that a core 16a is exposed. The connector 12 is formed with a notch 12B at the base thereof. The exposed core 16a is located in the notch 12B.

Figure 4:
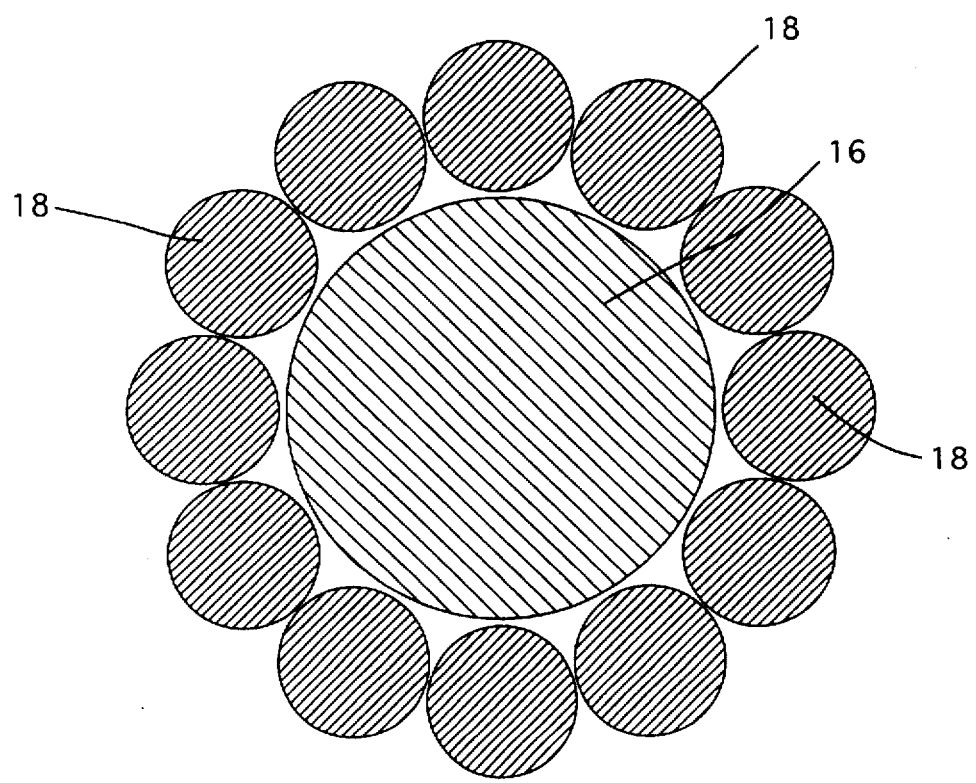
FIG. 4 is a view taken along the line VI—VI in FIG. 3.

As shown in FIG. 4, the optical fiber bundles 18 are located annularly around the main optical fiber and a set ring 20 which is located around the optical fiber bundles 18 is disposed in said through-hole 12A.

Figure 3:
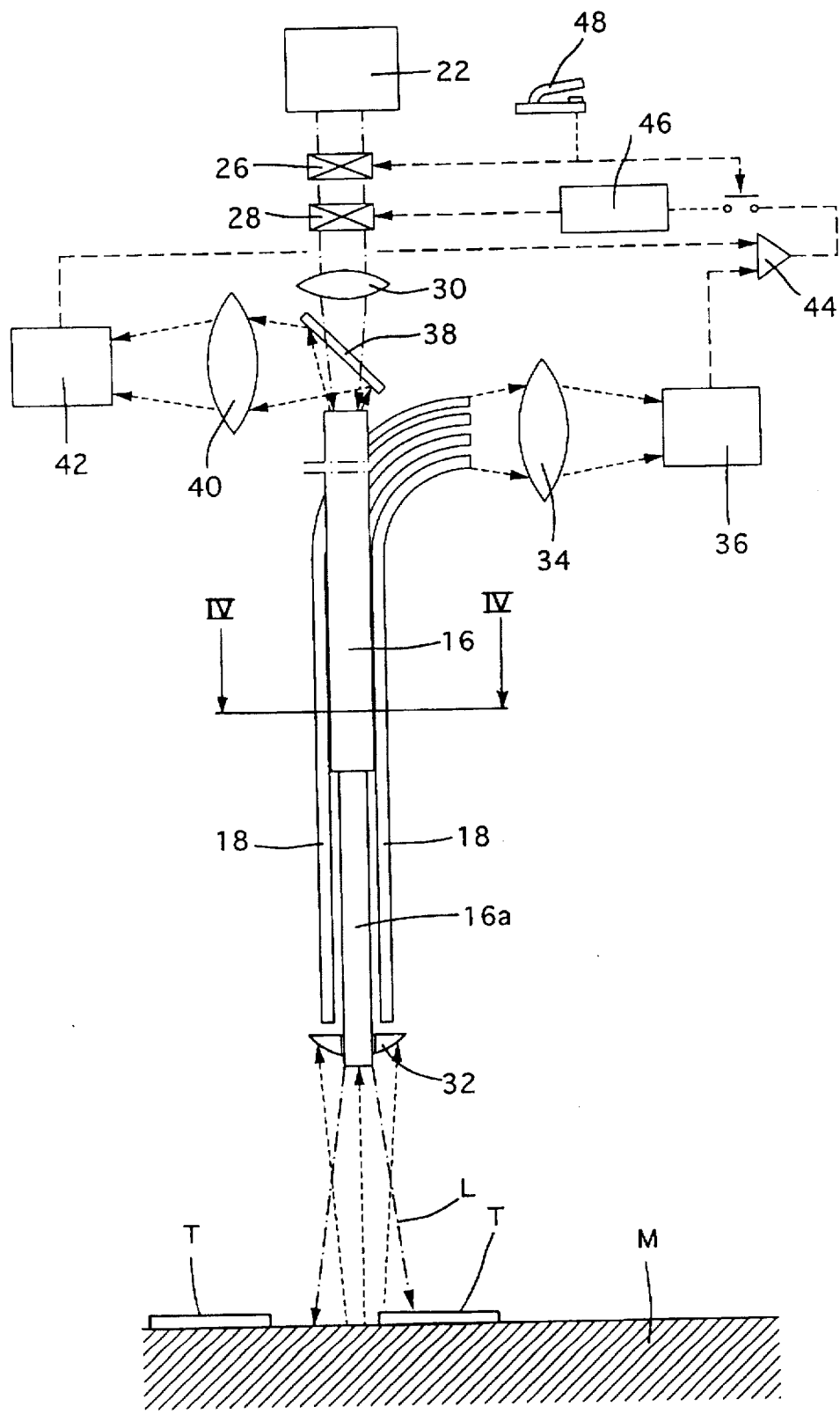
FIG. 3 is an explanatory view showing only an optical system which is extracted from the laser irradiating device of the present invention.

As shown in FIG. 3 in which only the optical elements are shown, the optical fiber 16 is optically coupled with a laser light generator 22. The laser light generator 22 is preferably capable of the generating pulsed laser light.

As shown in FIG. 1, the handpiece 10 is supplied with a cooling gas G such as cleaning gas or carbon dioxide from a compressed gas source 24. The gas G passes the notch 12 and a space between the inner surface of the through-hole 12A and the outer surface of the core 16a and then it is blown upon the target tissue M. Blowing of the gas is carried out for mitigating the burden upon a patient to be operated by removing the heat which is generated by the irradiation of the laser light L and for removal of the scattered material.

The front terminal fitting 14 is adapted to keep the distance between the laser light L emission tip end of the optical fiber 16 and the surface of the tissue M, for example the separation distance which falls within a range of 3 to 5 mm. In order to enable the operator to move the handpiece 10 to next position by sliding it along the surface of the tissue M, the metallic front terminal fitting 14 is integral with an abutting guide 14A made of a plastic material having a circular cross-section and an arcuate longitudinal section, which is excellent in sliding characteristics. The front terminal fitting 14 is formed with an opening 14a for purposes of discharging the gas externally and or confirming the laser light irradiation position.

On the other hand, as shown in FIG. 3, the laser light from the laser light generator 22 is passed through first and second laser light switches 26 and 28 and is incident upon the rear end of the main optical fiber 18 by an incidence lens 30. The laser light L is then passed through the main optical fiber 18 and is impinged upon the surface of the tissue M from the front end of the fiber 18.

In this case, a target material T is applied upon the surface of the tissue M. The target material T includes laser light absorbing powders which are dispersed in a dispersant. The target material T is liquid. The target material T preferably includes laser light absorbing powders having a particle size of not larger than 40 μm, which are dispersed in water and alcohol.

The target material T is applied on a target tissue, for example, the nevus to be eliminated with a felt pen. The laser light L which has transmitted through the main optical fiber 16 is emitted toward the target applied are.

The laser light L which has collided with the target material T will be absorbed by the laser light absorbing powders contained in the target material T so that it will be converted into thermal energy. As a result, the temperature of the laser light irradiated tissue elevates momentarily to high temperatures such as 800° to 1000° C., so that vaporization of the tissue takes place. If the vaporization of the tissue is not sufficient by one shot of the laser light, irradiation of the laser light is conducted again after application of the target material. The number of repetitions of application of the target material and the laser light irradiation can be properly selected.

In order to enable the operator to conduct treatment while visually monitoring the manner of irradiation of the target material T with the laser light, an O-ring 21 is provided between the base end of the front terminal fitting 14 and a flange of the connector 12, which serves to stably secure the front end fitting 14 relative to the connector 12 after the angular position of the front terminal fitting 14 around its axis has been adjusted.

The target material includes laser light absorbing powders having a particle size of not larger than 40 μm, more preferably 10 μm. If the particles size becomes larger, it is more difficult to properly disperse the powders in a dispersing medium and the film of the applied target material will have a larger thickness and a smooth surface of the film is not obtained, resulting in nonuniform vaporization of the tissue on irradiation with laser light.

The dispersing agent may include water, in particular sterilized water. It is preferable to add alcohol the dispersing medium. The alcohol may include methyl alcohol, ethyl alcohol, propyl alcohol, butyl alcohol. Addition of the alcohol enables the target material to be prematurely dried when the target material is irradiated with laser light since the alcohol is vaporized so that latent heat is removed due to vaporization. The dispersing medium may be added with anionic, nonionic, cationic surface-active agents as well as soap, such as pulverized medical soap in order to increase the dispersion properties. The surface-active agent or soap will provide an effect that the target material can be applied on the tissue to form a uniform film.

The laser light absorbing powders are not limited as far as they absorb the laser light to generate heat. The powder material may include carbon, manganese dioxide and iron oxides and a combination thereof. Since these materials can be applied to a desired position on the surface of the tissue while visually monitored and the laser irradiation point on the target can be confirmed.

Figure 5:
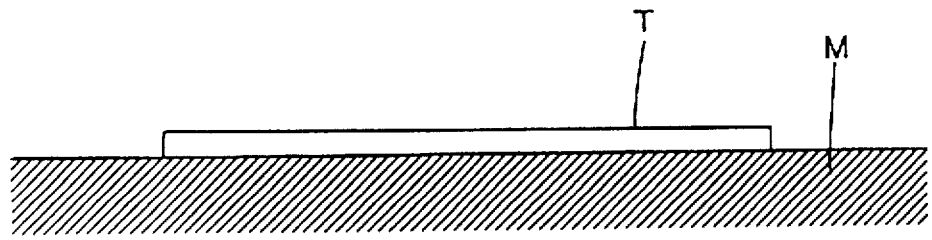
FIG. 5 is a schematic view showing the application condition of the target material.
Figure 6:
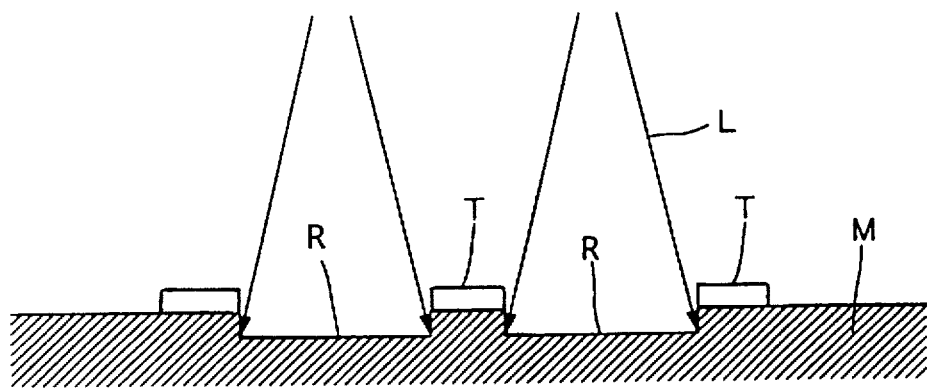
FIG. 6 is a schematic view showing the first laser light irradiated condition.
Figure 7:
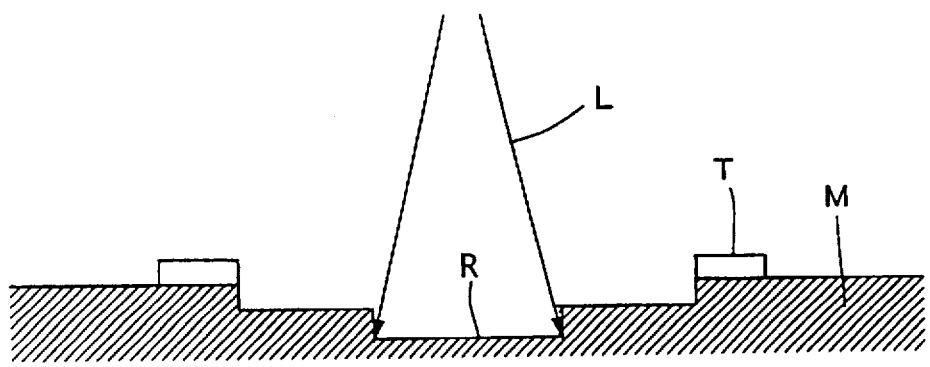
FIG. 7 is a schematic view showing the second laser light irradiated condition.
Figure 8:
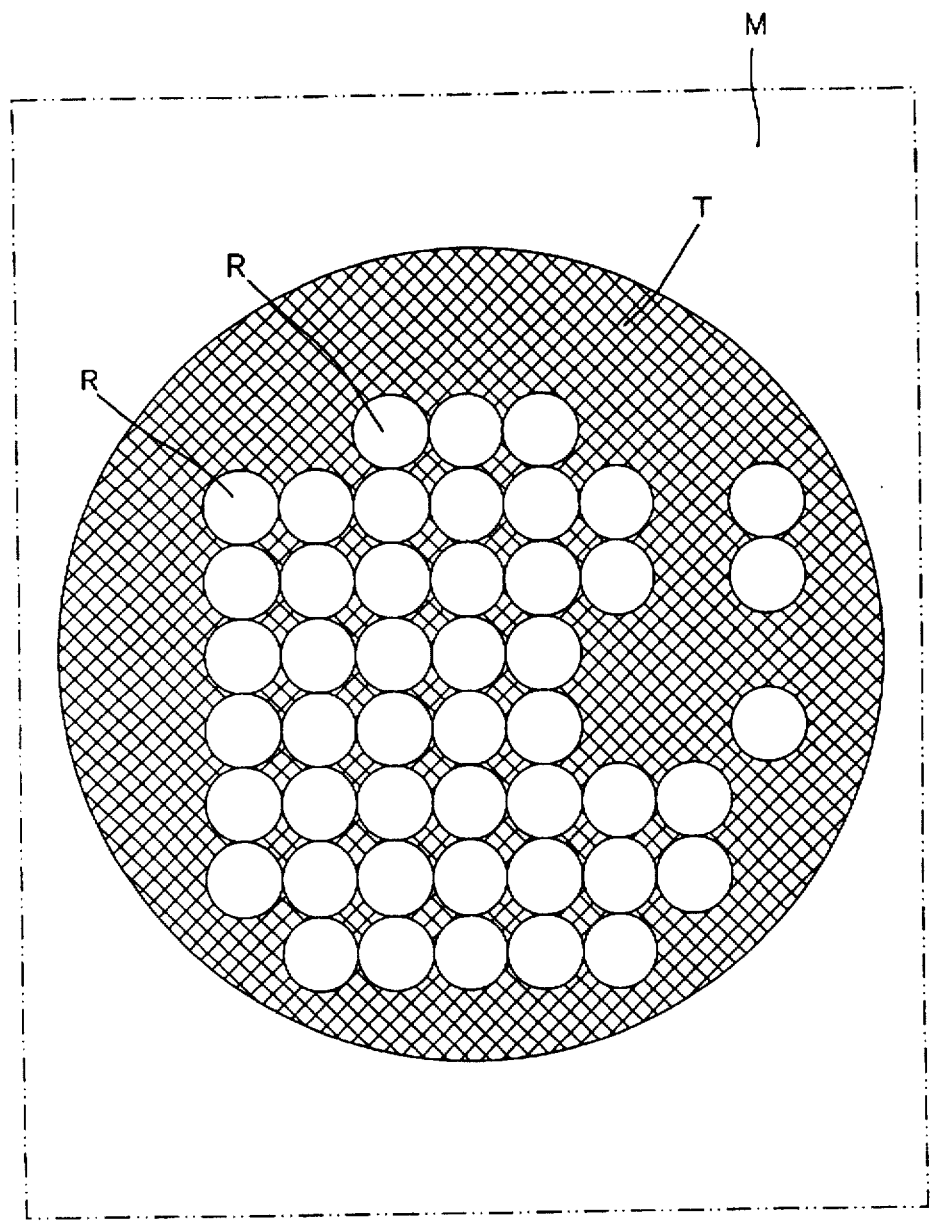
FIG. 8 is an explanatory view showing the relation between the target material applied area and the laser light irradiated area.

As shown in FIGS. 1 and 5, the target material T is applied on a given position on the tissue. The entire of the target T is irradiated with the laser light. The original skin condition can be viewed at the irradiated spots while the target material which has black color remains at the unirradiated spots as shown in FIGS. 6 and 8. An operator can determine that the black area has not been irradiated and then conduct laser light irradiation of the black area at next stage as shown in FIG. 7. This enables the operator to easily conduct the laser light irradiation over the entire desired area.

The liquid target material T may include alcohol and water at ratios of 0.5 to 10 and 3 to 25, respectively for laser light absorbing powders. The liquid target may have a viscosity of 2 to 200 CPS (20° C.). It is preferable that the liquid target have approximately same viscosity as that of milk to provide uniformity of the film.

Use of Nd:YAG laser light is more preferable than that of carbon dioxide gas laser light. It is preferable that the laser light be pulsed laser light having a pulse interval of 5 to 50 PPS at 10 to 500 mJ.

On the other hand, the irradiated area R usually has a diameter of 1 to 5 mm depending upon the diameter of the tip end face of the main optical fiber and the separation distance between its front end face and the surface of the tissue M. Accordingly, the unirradiated area which is surrounded by the irradiated areas R, R as shown in FIGS. 6 and 8 is so small that it is hard to visually observe. Even if the unirradiated area can be visually observed, positioning of the tip end face of the main optical fiber 18 upon its unirradiated area will impose a great burden upon the operator.

In the present invention, there is provided means for optically determining the absence or presence of the target material T or the proportion of the target material with respect to a given area.

As shown in FIGS. 1 and 3, a condenser lens 32 is provided on the side of the front end of the optical fiber bundles 18 so that the laser light which has been reflected on a given area of the surface of the tissue M is condensed and is made incident to each of the optical fiber bundles 18. The reflected light emitted from the rear end faces of the fiber bundle 18 is passed through a convergence lens 23 so that it is incident upon a second light quantity measuring photocell 36 for measuring the quantity of light.

The laser light which has been reflected on the surface of the tissue M is also incident upon the main optical fiber 18. Accordingly, visual light is extracted from the reflected light emitted from the rear end face of the main optical fiber 18 by a half mirror 38 which transmits the laser light and reflects visual light. The extracted visual light is passed through a convergence lens 40 and is incident upon a first light quantity measuring photocell 42 for measuring the quantity of the reflected light.

In such an arrangement, a second quantity of light Im which is detected by the second light quantity measuring means to a first quantity of light Ir which is detected by the first light quantity measuring means by an comparator 44 to provide the ratio (Im/Ir) as an index representing whether or not unirradiated area is present or reirradiation is necessary. When it is determined that irradiation with laser light is necessary, the second laser light switch 28 is energized (made open) by an irradiation control means 48 so that the laser light from the laser light generator 22 is incident upon the main optical fiber 16. The first laser light switch 26 is made open by the actuation of a foot switch 48 which is actuated when the operation is started or resumed after its interruption. If the second laser light switch 28 is closed even when the first laser light switch 26 is opened by the actuation of the foot switch 48, the laser light is not incident upon the main optical fiber 18. As mentioned above, the second laser light switch 28 is made open under a given condition of the ratio of the reflected light quantities (Im/Ir).

In the embodiment, the separation distance between the front end of the fiber 16 and the surface of the tissue M is selected by adjusting the position of the main optical fiber 16 so that the area irradiated with the laser from the main optical fiber is larger than the target tissue area, the light from which is condensed by the condenser lens 32 as shown in FIG. 3. Accordingly, the relation between the first quantity of light which is detected by the first light quantity measuring means 42 via the main optical fiber 16 and the second quantity of light Im which is detected by the second light quantity measuring means 38 via the fiber bundles 18 is as follows:

Im≈Ir if there is a target material T or no target material T over an entire of the laser light irradiated area. Since Im<Ir if there is an unirradiated area as shown in FIGS. 3 and 8, the ratio of the quantities of reflected light is less than 1.0. Therefore, irradiation with laser light can be conducted by opening the second laser light switch 28 if a condition of Im/Ir<1.0 is satisfied. Excessive irradiation may occur. Accordingly, it is preferable that a proper laser light irradiation condition value F which is in the range of 0 to 1.0 is preliminarily determined and irradiation of laser light is conducted by opening the second optical switch 28 if the condition of (Im/Ir)<F is satisfied.

Thus, the operator grips the handpiece 10 and then turns a foot switch 48 on and slides the front end of the handpiece 10 along the target material T coated surface of the tissue. Irradiation with laser light is conducted by opening the second laser light switch 28 under condition of (Im/Ir)<F. If irradiation with laser light is conducted again if necessary, areas which have not been irradiated with laser light on a first trial are irradiated with laser light.

Figure 9:
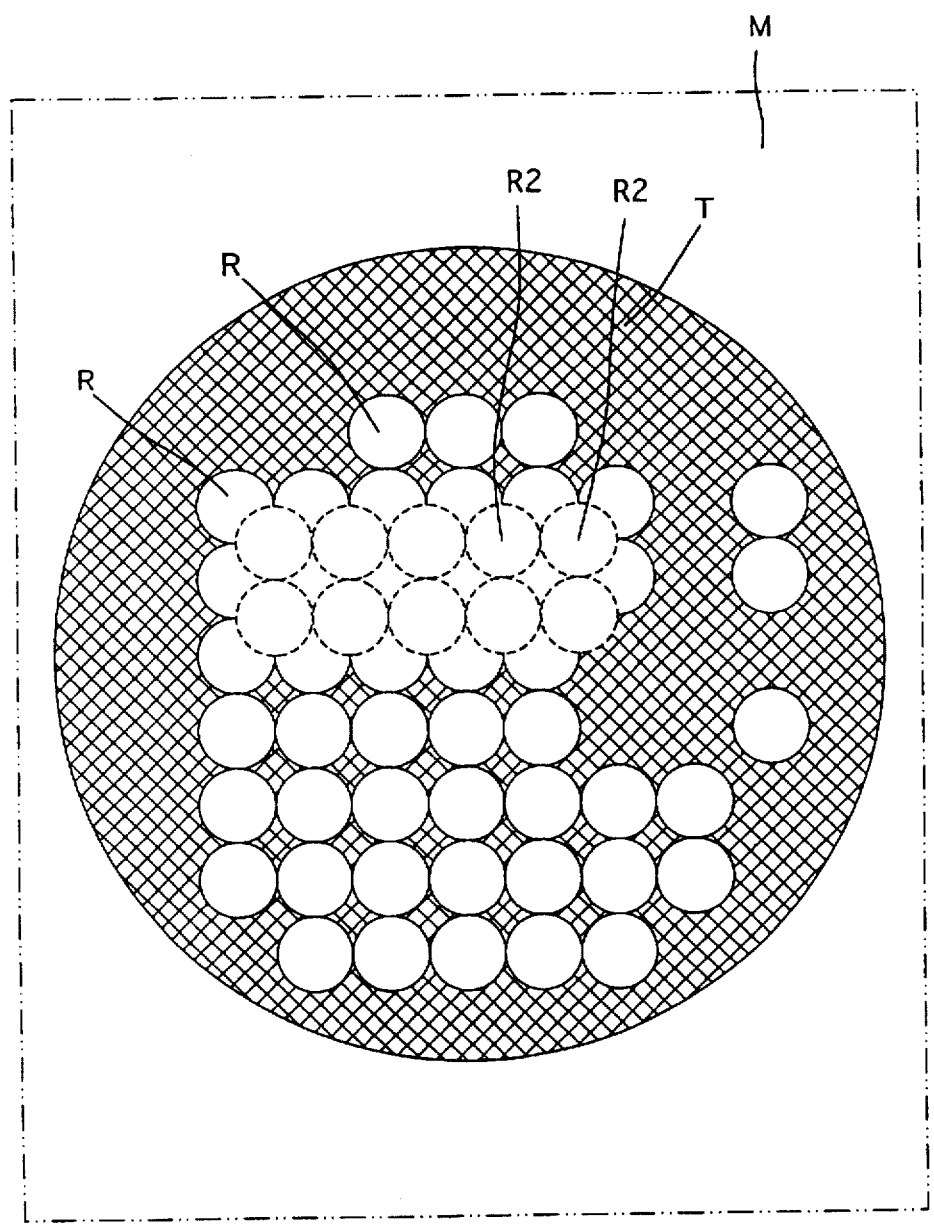
FIG. 9 is an explanatory view showing the relation between the target material applied area and the laser light irradiation area in a case in which the irradiating device of the present invention is used.

The areas which are irradiated with laser light on a second trial are represented at R2 in FIG. 9. In such a manner, occurrence of unirradiated area is prevented.

Figure 10:
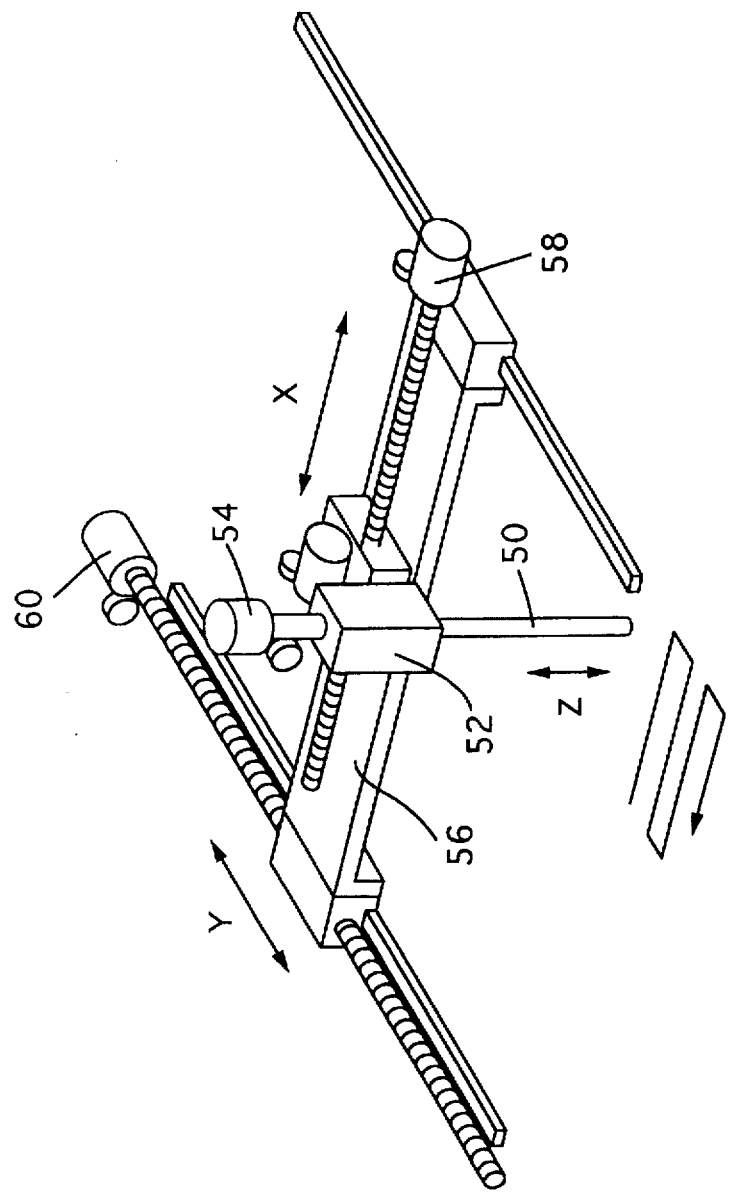
FIG. 10 is a schematic perspective view showing a probe operating mechanism of the present invention.
Figure 11:
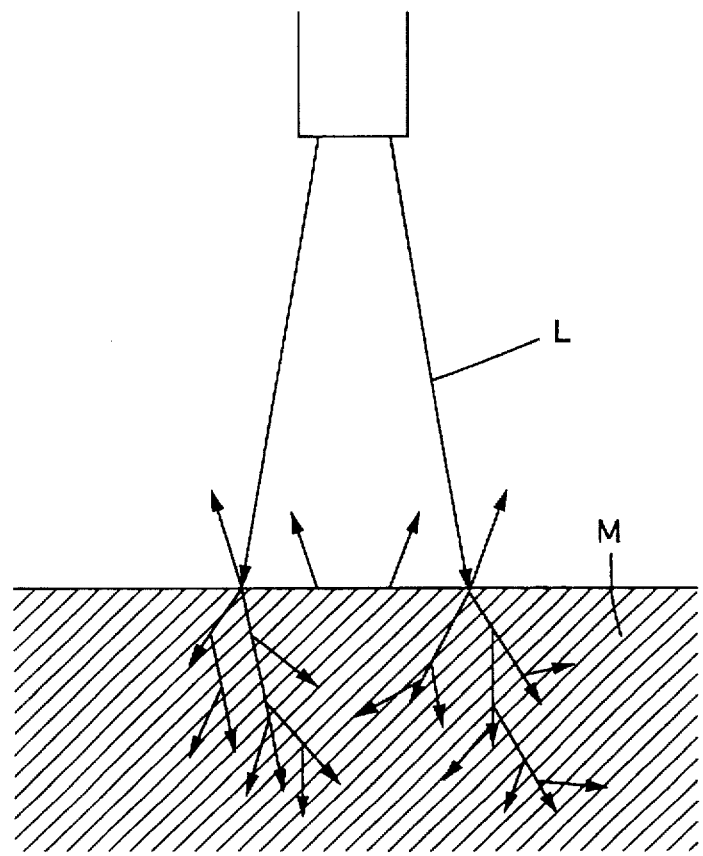
FIG. 11 is an explanatory view of the condition of the scattering of the laser light without using any target material.

Although the operator moves the handpiece while gripping it in this embodiment, the movement of the handpiece can be automated in a manner as shown in FIG. 10. In other words, a holder 50 comprising main optical fiber 16 and optical fiber bundles 18, which corresponds to the handpiece 8 is supported by a holder fitting 52 so that it is movable in a Z direction by a Z-direction drive motor 54. The holder fitting 52 is movable along an X direction guide 56 by an X direction drive motor 58. The X direction guide 56 is movable in a Y direction by a Y direction drive motor 60.

A moving device for the holder fitting 52 of such a X-Y translating apparatus is positioned to face the surface of the patient tissue. The holder 50 can be scanned as shown in FIG. 10. If the irradiation area is small, it is not necessary to move the holder 50 in a Z direction since the tissue surface is substantially flat.

Although the present invention has been described by way of example of elimination of the nevus on the skin, it may be applied for discoloring of tatoo and elimination of skin lines as well as treatment of athlete's foot. In the field of surgery the target is applied on the dental tissue to achieve the removal of that portion.

On the other hand, in the present invention, it is not essential to preliminarily apply the target material on the tissue surface. In other words, the nevus portion exhibits a dark color different from the other area. Accordingly, there is a difference between Im and Ir even if any target material is not applied. Therefore, the principle of the present invention is applicable without applying the target material.

What is claimed is:

1. A laser treating apparatus for modifying the surface of living tissue by irradiating it with laser light comprising:
   a laser light generator;
   a laser light transmitting means for receiving the laser light from said laser light generator to impinge the laser light upon the surface of the tissue;
   switching means between said laser light generator and said laser light transmitting means;
   a first light quantity detecting means for measuring the quantity of light (Ir) which has been emitted from said laser light transmitting means and has been reflected from the surface of the tissue;
   second light quantity detecting means for measuring the quantity of laser light (Im) reflected from a predetermined area on said surface of the tissue; and
   irradiation control means for impinging the laser light from said laser light generator upon said laser light transmitting means by actuating said switching means when the irradiation of laser light is determined necessary based upon the ratio (Im/Ir) of the second light quantity Im measured by said second light quantity detecting means to the first light quantity Ir measured by said first light quantity detecting means which is used as an index representing whether or not an unirradiated area is present, and thus whether irradiation is necessary.

2. A laser treating apparatus for modifying the surface of living tissue by irradiating it with laser light comprising:
   a laser light generator;
   a laser light transmitting means comprising a main optical fiber for receiving the laser light from said laser light generator to irradiate the surface of the living tissue with the laser light;
   a plurality of optical fiber bundles which are annularly disposed around the main optical fiber and having the front ends facing the surface of the tissue;
   laser light switching means between said laser light generator and said laser light transmitting means;
   a first light quantity detecting means for measuring the quantity light (Ir) which has been emitted from said laser light transmitting means and has been reflected from the surface of the tissue;
   second light quantity detecting means for measuring the quantity of laser light (Im) reflected from a predetermined area on said surface of the tissue; and
   irradiation control means for impinging the laser light from said laser light generator upon said laser light transmitting means by actuating said switching means when the irradiation of laser light is determined necessary based upon the ratio (Im/Ir) of the second light quantity Im measured by said second light quantity detecting means to the first light quantity detecting means which is used as an index representing whether or not an unirradiated area is present, and thus whether irradiation is necessary.

3. A laser treating apparatus as defined in claim 2 in which first and second laser light switching means are provided between said laser light generator and said laser light transmitting means, said first laser light switching means being actuated in association with a foot switch for an operator, said second laser light switching means being actuated by said irradiation control means.

4. A laser treating apparatus as defined in claim 2 in which a condenser lens for condensing the reflected laser light (Im) to said optical fiber bundles is provided adjacent the front ends of said optical fiber bundles.

5. A laser treating apparatus as defined in claim 4 in which said condenser lens is formed with a central through-hole, into which said main optical fiber is inserted.

6. A laser treating apparatus as defined in claim 2 in which said main optical fiber and said optical fiber bundles are secured to a holder which is held by an operator.

7. A laser treating apparatus as defined in claim 6 in which said main optical fiber is movably supported by the holder so that the separation distance between the optical fiber and said tissue surface is adjustable.

8. A laser treating apparatus as defined in claim 2 in which said main optical fiber and said optical fiber bundles are secured to the holder, said holder being held in a holder fitting of an X-Y translating apparatus, which holder fitting is movable on a plane parallel with the surface of the tissue.

9. A laser treating apparatus as defined in claim 1 in which a target material comprising laser light absorbing powders having a particle size of 40 µm or less which are dispersed in a dispersing medium is applied to a coating thickness of 40 µm or less on the surface of said tissue.

10. A laser treating apparatus as defined in claim 2 in which a target material comprising laser light absorbing powders having a particle size of 40 µm or less which are dispersed in a dispersing medium is applied to a coating thickness of 40 µm or less on the surface of said tissue.

* * * * *